(12) United States Patent
Muranaka et al.

(10) Patent No.: US 10,435,564 B2
(45) Date of Patent: Oct. 8, 2019

(54) RHODAMINE-BASED COLORANT COMPOUND AND PROCESS FOR PRODUCING SAME

(71) Applicant: RIKEN, Saitama (JP)

(72) Inventors: Atsuya Muranaka, Saitama (JP); Yoshinao Shirasaki, Saitama (JP); Masanobu Uchiyama, Saitama (JP); Shinichiro Kamino, Saitama (JP)

(73) Assignee: RIKEN, Saitama (JP)

( * ) Notice: Subject to any disclaimer, the term of this patent is extended or adjusted under 35 U.S.C. 154(b) by 0 days.

(21) Appl. No.: 15/754,495

(22) PCT Filed: Sep. 2, 2016

(86) PCT No.: PCT/JP2016/075850
§ 371 (c)(1),
(2) Date: Feb. 22, 2018

(87) PCT Pub. No.: WO2017/038987
PCT Pub. Date: Mar. 9, 2017

(65) Prior Publication Data
US 2018/0244923 A1 Aug. 30, 2018

(30) Foreign Application Priority Data
Sep. 3, 2015 (JP) ................. 2015-173779

(51) Int. Cl.
| C09B 11/24 | (2006.01) |
| C07D 491/22 | (2006.01) |
| C07D 493/22 | (2006.01) |
| C09K 11/06 | (2006.01) |
| C09B 11/28 | (2006.01) |

(52) U.S. Cl.
CPC ............ *C09B 11/24* (2013.01); *C07D 491/22* (2013.01); *C07D 493/22* (2013.01); *C09B 11/28* (2013.01); *C09K 11/06* (2013.01)

(58) Field of Classification Search
CPC ..... C09B 11/24; C07D 491/22; C07D 493/22; C07B 11/28
USPC ....................................... 549/227
See application file for complete search history.

(56) References Cited

U.S. PATENT DOCUMENTS

| 3,663,571 A | * | 5/1972 | Kimura | ............... B41M 5/1455 549/224 |
| 6,169,185 B1 | * | 1/2001 | Likavec | ............... C07D 407/04 548/305.1 |
| 8,134,017 B1 | | 3/2012 | Riken | |
| 2006/0204990 A1 | | 9/2006 | Lukhtanov et al. | |
| 2009/0265866 A1 | | 10/2009 | Eliu et al. | |
| 2013/0096309 A1 | | 4/2013 | Bremberg et al. | |

FOREIGN PATENT DOCUMENTS

| CN | 104479670 | 4/2015 |
| EP | 1934291 | 6/2008 |
| EP | 1991705 | 11/2008 |
| EP | 2552492 | 2/2013 |
| GB | 2314329 | 12/1997 |
| JP | 47-19799 | 6/1972 |
| JP | H01-190484 A | 7/1989 |
| JP | 10-7632 | 1/1998 |
| JP | 2003-31273 | 1/2003 |
| JP | 2009-513753 | 4/2009 |
| JP | 2009-527591 | 7/2009 |
| JP | 2013-523964 | 6/2013 |
| JP | 2014-5422 | 1/2014 |
| WO | WO 2007/039502 | 4/2007 |
| WO | WO 2007/098336 | 8/2007 |
| WO | WO 2011/123820 | 10/2011 |
| WO | WO 2014/002292 | 1/2014 |

OTHER PUBLICATIONS

Kamino, S. et al., A red-emissive aminobenzopyrano-xanthene dye: elucidation of fluorescence emission mechanisms in solution and in the aggregate state, Phys. Chem. Chem. Phys., 2013, 15, 2131-2140. Accepted Dec. 5, 2012.
Extended European Search Report dated Mar. 4, 2019 for the corresponding European Patent Application No. 16842016.4.

* cited by examiner

*Primary Examiner* — Rita J Desai
(74) *Attorney, Agent, or Firm* — Leason Ellis LLP

(57) ABSTRACT

Provided is a compound capable of exhibiting different changes in hue with one kind of molecule. The compound has julolidine structures, and is represented by a general formula (1):

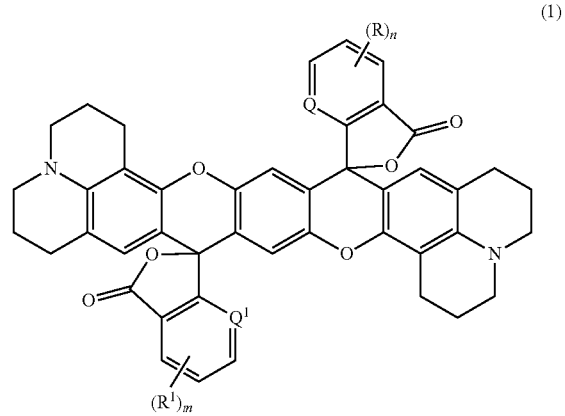

wherein each of Q and $Q^1$ represents C(R) or N; R represents a hydrogen atom, a halogen atom, an alkyl group having 1 to 6 carbon atoms, or a carboxyl group, where two Rs may bind to each other to form a ring; $R^1$ represents a hydrogen atom, a halogen atom, an alkyl group having 1 to 6 carbon atoms, or a carboxyl group, where two $R^1$s may bind to each other to form a ring; n represents a number of 0 to 3; and m represents a number of 0 to 3.

6 Claims, 3 Drawing Sheets

RHODAMINE-BASED COLORANT COMPOUND AND PROCESS FOR PRODUCING SAME

CROSS-REFERENCE TO RELATED PATENT APPLICATIONS

This application is a U.S. National Phase Application under 35 U.S.C. § 371 of International Patent Application No. PCT/JP2016/075850, filed Sep. 2, 2016, which claims the priority of Japanese Application No. 2015-173779, filed Sep. 3, 2015, which is incorporated by reference as if expressly set forth in its entirety herein.

TECHNICAL FIELD

The present invention relates to a rhodamine-based colorant compound and a method for producing the same.

BACKGROUND ART

As a fluorescent colorant compound, various derivatives of rhodamine have been studied. In addition, as a compound prepared by condensing two rhodamine molecules, there has been known an aminobenzopyrano-xanthene colorant compound (Patent document 1). It is known that this aminobenzopyrano-xanthene compound exhibits three types of molecular structures which are a neutral form, a monocationic form and a dicationic form, depending on the hydrogen-ion concentration of a solution, and that each molecular structure leads to different absorption and emission properties (Non-patent document 1).

PRIOR ART DOCUMENT

Patent Document

Patent document 1: Specification of U.S. Pat. No. 8,134,017

Non-Patent Document

Non-patent document 1: Shinichiro Kamino et al., "A red-emissive aminobenzopyrano-xanthene dye: elucidation of fluorescence emission mechanisms in solution and in the aggregate state", Physical Chemistry Chemical Physics, 2013, 15, p. 2131-2140

SUMMARY OF THE INVENTION

Problem to be Solved by the Invention

However, since there are only small differences in absorption and emission properties between the monocationic form and the dicationic form, there has been a problem that changes in hue cannot be clearly exhibited.
Therefore, it is an object of the present invention to provide a compound capable of exhibiting different changes in hue with one kind of molecule.

Means to Solve the Problem

The inventors of the present application diligently conducted a series of studies to solve the aforementioned problem, and arrived at the present invention as follows. That is, the inventors found that the following compound was able to solve the above problem.

Specifically, the present invention is to provide the invention below.

[1]
A compound having julolidine structures, represented by a general formula (1):

[Chemical formula 1]

(1)

wherein Q represents C(R) or N; $Q^1$ represents $C(R^1)$ or N; R represents a hydrogen atom, a halogen atom, an alkyl group having 1 to 6 carbon atoms, or a carboxyl group, where two Rs may bind to each other to form a ring; $R^1$ represents a hydrogen atom, a halogen atom, an alkyl group having 1 to 6 carbon atoms, or a carboxyl group, where two $R^1$s may bind to each other to form a ring; n represents a number of 0 to 3; and m represents a number of 0 to 3.

[2]
The compound according to [1], wherein Q and $Q^1$ in the general formula (1) respectively represent C(R) and $C(R^1)$.

[3]
The compound according to [1], wherein each of Q and $Q^1$ in the general formula (1) represents N.

[4]
A compound represented by a general formula (2):

[Chemical formula 2]

(2)

wherein each of $Q^2$ and $Q^3$ represents C(R) or N; R represents a hydrogen atom, a halogen atom, an alkyl group having 1 to 6 carbon atoms, or a carboxyl group; $R^2$ represents a halogen atom, an alkyl group having 1 to 6 carbon atoms, or a carboxyl group, where two $R^2$s may bind to each other to form a ring; $R^3$ represents a halogen atom, an alkyl group having 1 to 6 carbon atoms, or a carboxyl group, where two $R^3$s may bind to each other to form a ring; p represents a number of 1 to 3; q represents a number of 1 to 3; and each of $R^4$ and $R^5$ represents a hydrogen atom or an alkyl group having 1 to 6 carbon atoms.

[5]

The compound according to [4], wherein each of $R^2$ and $R^3$ in the general formula (2) represents a carboxyl group.

[6]

The compound according to [4], wherein in the general formula (2), two $R^2$s are bound together to form a benzene ring, and two $R^3$s are bound together to form a benzene ring.

[7]

A compound represented by a general formula (2'):

[Chemical formula 3]

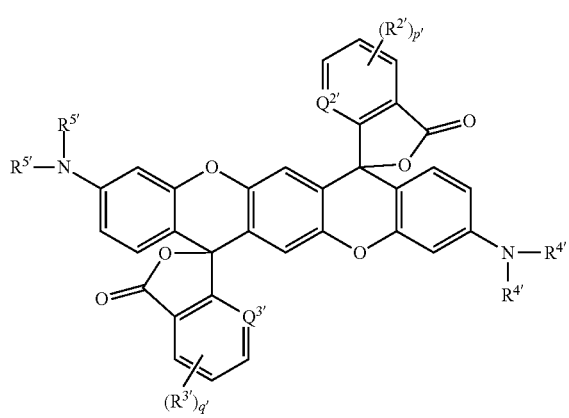

(2')

wherein each of $Q^{2'}$ and $Q^{3'}$ represents C(R') or N; R' represents a hydrogen atom, a halogen atom, an alkyl group having 1 to 6 carbon atoms, or a carboxyl group; $R^{2'}$ represents a hydrogen atom, a halogen atom, an alkyl group having 1 to 6 carbon atoms, or a carboxyl group, where two $R^{2'}$s may bind to each other to form a ring; $R^{3'}$ represents a hydrogen atom, a halogen atom, an alkyl group having 1 to 6 carbon atoms, or a carboxyl group, where two $R^{3'}$s may bind to each other to form a ring; p' represents a number of 0 to 3; q' represents a number of 0 to 3; each of $R^{4'}$ and $R^{5'}$ represents a hydrogen atom or an alkyl group having 6 to 12 carbon atoms.

[8]

A reagent for detecting phenols, comprising a compound represented by a general formula (3):

[Chemical formula 4]

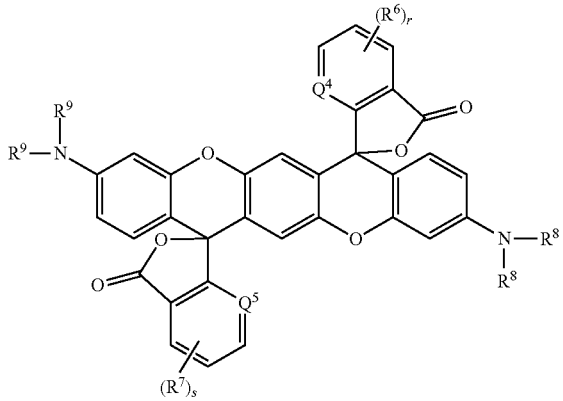

(3)

wherein each of $Q^4$ and $Q^5$ represents C(R) or N; R represents a hydrogen atom, a halogen atom, an alkyl group having 1 to 6 carbon atoms, or a carboxyl group; $R^6$ represents a halogen atom, an alkyl group having 1 to 6 carbon atoms, or a carboxyl group, where two $R^6$s may bind to each other to form a ring; $R^7$ represents a halogen atom, an alkyl group having 1 to 6 carbon atoms, or a carboxyl group, where two $R^7$s may bind to each other to form a ring; r represents a number of 0 to 3; s represents a number of 0 to 3; each of $R^8$ and $R^9$ may represent a hydrogen atom or an alkyl group having 1 to 6 carbon atoms, or $R^8$s or $R^9$s may form a julolidine structure together with a nitrogen atom bonded thereto and a benzene ring adjacent to the nitrogen atom.

[9]

A method for producing a compound represented by a general formula (6), comprising:

obtaining a compound represented by a general formula (5) by reacting 8-hydroxyjulolidine with a compound represented by a general formula (4); and reacting the compound represented by the general formula (5) with hydroquinone in the presence of a condensing agent,

[Chemical formula 5]

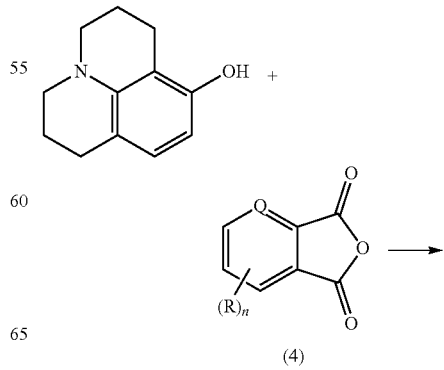

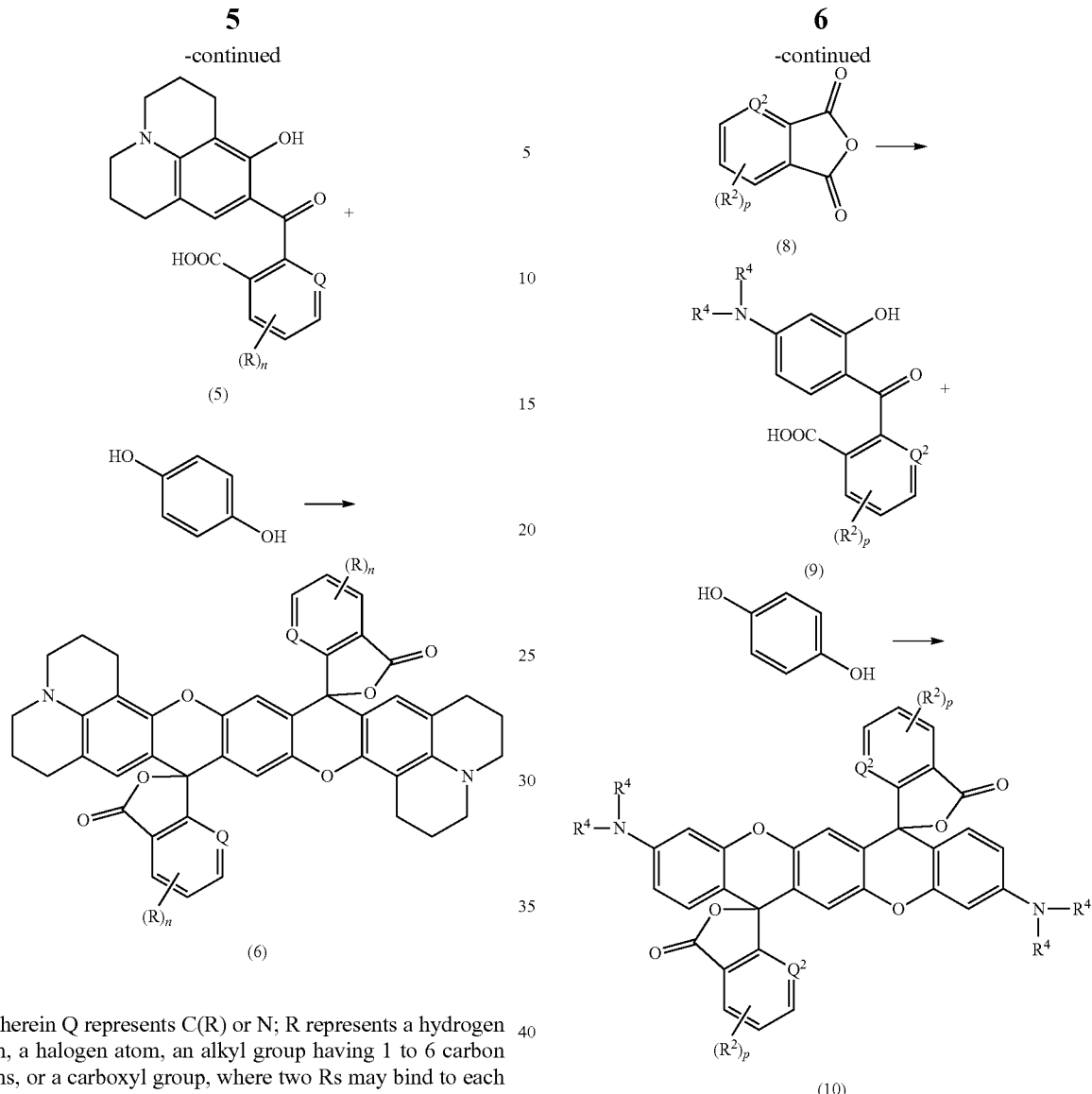

wherein Q represents C(R) or N; R represents a hydrogen atom, a halogen atom, an alkyl group having 1 to 6 carbon atoms, or a carboxyl group, where two Rs may bind to each other to form a ring; and n represents a number of 0 to 3.

[10]

A method for producing a compound represented by a general formula (10), comprising:

obtaining a compound represented by a general formula (9) by reacting a compound represented by a general formula (7) with a compound represented by a general formula (8); and reacting the compound represented by the general formula (9) with hydroquinone in the presence of a condensing agent,

[Chemical formula 6]

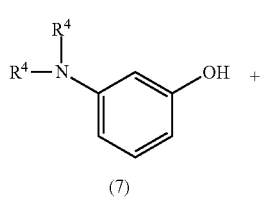

(7)

wherein $Q^2$ represents C(R) or N; R represents a hydrogen atom, a halogen atom, an alkyl group having 1 to 6 carbon atoms, or a carboxyl group; $R^2$ represents a halogen atom, an alkyl group having 1 to 6 carbon atoms, or a carboxyl group, where two $R^2$s may bind to each other to form a ring; p represents a number of 1 to 3; and $R^4$ represents a hydrogen atom or an alkyl group having 1 to 6 carbon atoms.

EFFECTS OF THE INVENTION

According to the present invention, there is provided a compound capable of exhibiting different changes in hue with one kind of molecule. Further, the compound of the invention is expected as a useful and novel compound, even in terms of a detection reagent.

MODE FOR CARRYING OUT THE INVENTION

Figure 1:
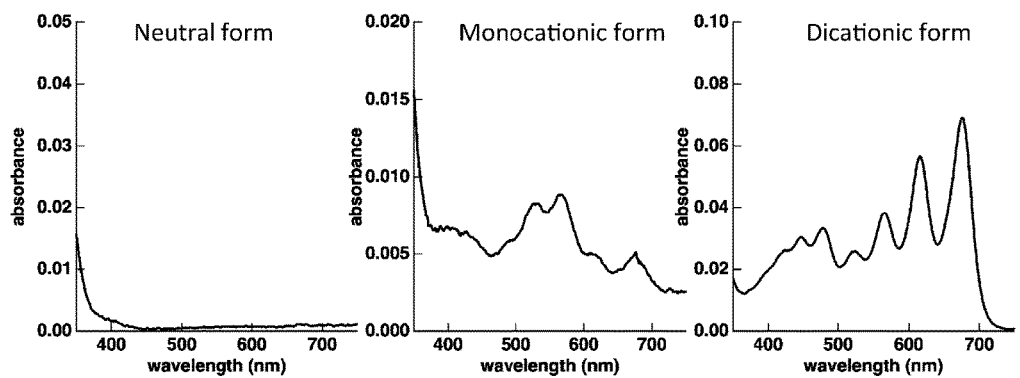
FIG. 1 is a diagram showing the absorption spectra of a compound obtained in working example 1.

The invention is described in detail hereunder.

A compound of the invention is represented by the following general formula (1).

[Chemical formula 7]

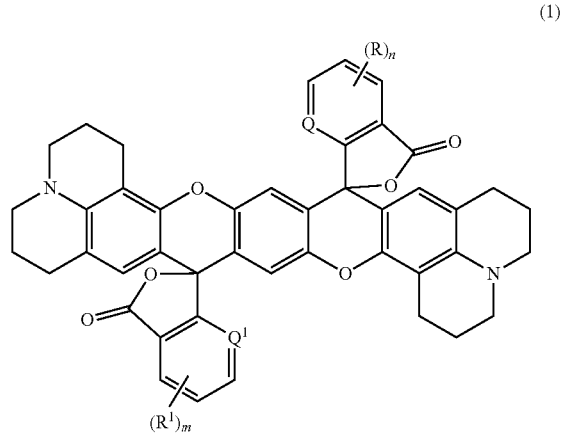

(1)

In the general formula (1), Q represents C(R) or N; $Q^1$ represents $C(R^1)$ or N; R represents a hydrogen atom, a halogen atom, an alkyl group having 1 to 6 carbon atoms, or a carboxyl group, where two Rs may bind to each other to form a ring; $R^1$ represents a hydrogen atom, a halogen atom, an alkyl group having 1 to 6 carbon atoms, or a carboxyl group, where two $R^1$s may bind to each other to form a ring; n represents a number of 0 to 3; and m represents a number of 0 to 3.

Examples of the halogen atoms represented by R and $R^1$ in the general formula (1) include a fluorine atom, a chlorine atom, a bromine atom and an iodine atom. Further, the alkyl group having 1 to 6 carbon atoms may be either linear or branched, a cycloalkyl group and a bicycloalkyl group. Specific examples of such alkyl group include a methyl group, an ethyl group, a propyl group, an isopropyl group, an n-butyl group, an isobutyl group, an s-butyl group, a t-butyl group, a pentyl group and a hexyl group. When there are multiple Rs or multiple $R^1$s, the Rs may be identical to or different from one another, and the $R^1$s may be identical to or different from one another as well.

By exchange of hydrogen ions, the compound represented by the general formula (1) may exhibit three types of structures which are a neutral form, a monocationic form and a dicationic form that are shown below.

[Chemical formulae 8]
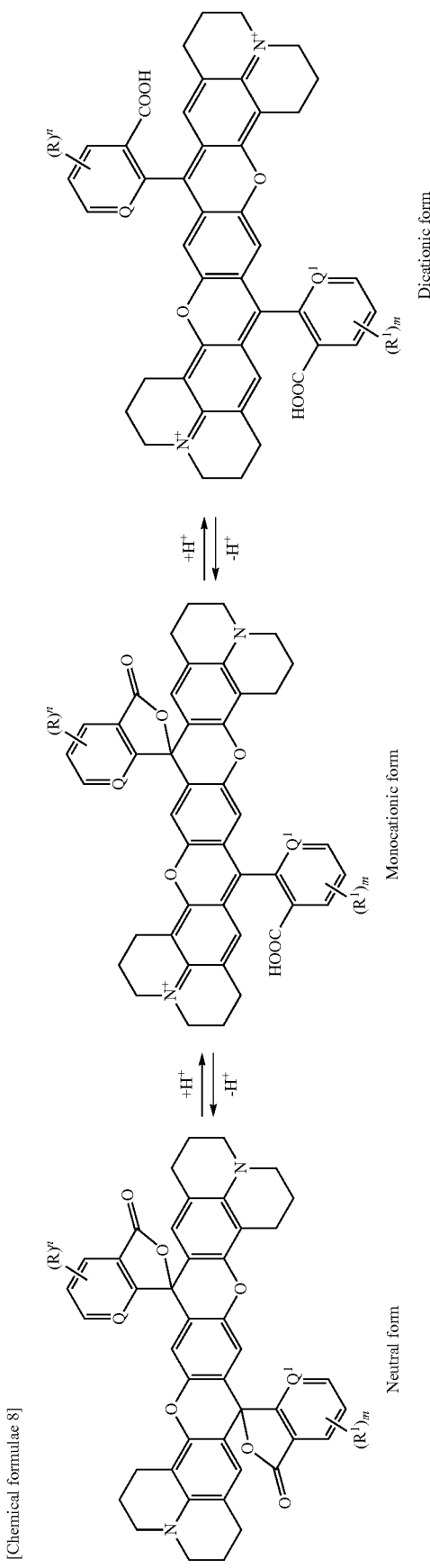

In the present invention, the compound represented by the general formula (1) includes these three types of structures.

The compound of the invention that is represented by the general formula (1) can be produced by the following method.

That is, a compound represented by a general formula (5) is obtained by reacting 8-hydroxyjulolidine with a compound represented by a general formula (4). Next, the compound represented by the general formula (5) is reacted with hydroquinone in the presence of a condensing agent.

[Chemical formula 9]

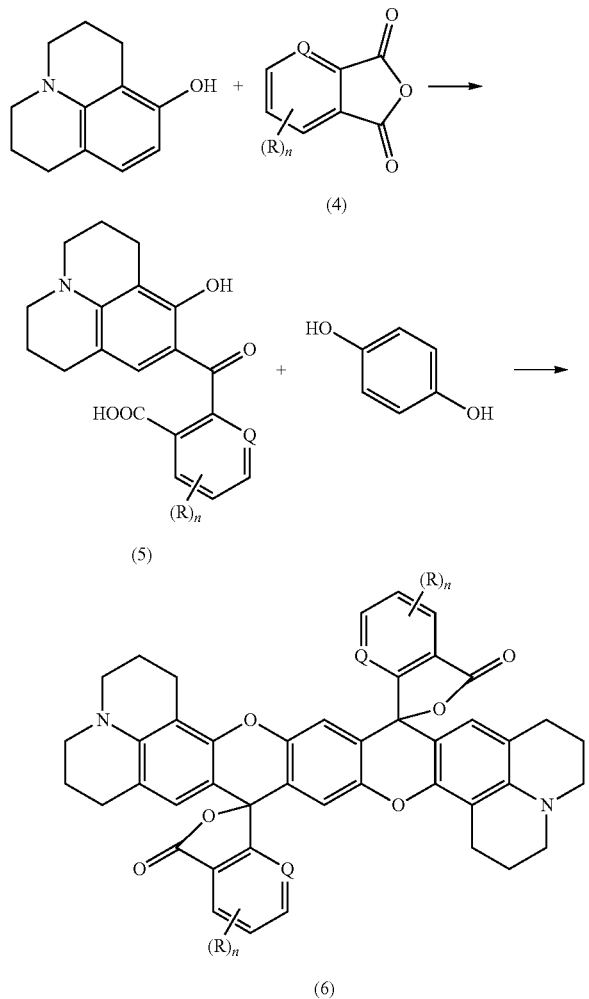

In the general formulae (4) to (6), Q represents C(R) or N; R represents a hydrogen atom, a halogen atom, an alkyl group having 1 to 6 carbon atoms, or a carboxyl group, where two Rs may bind to each other to form a ring; and n represents a number of 0 to 3.

Examples of the halogen atom represented by R include a fluorine atom, a chlorine atom, a bromine atom and an iodine atom. Further, examples of the alkyl group having 1 to 6 carbon atoms include groups similar to those in the general formula (1). When there are multiple Rs, they may be either identical to or different from one another.

Following are specific examples of the compound represented by the general formula (4).

[Chemical formulae 10]

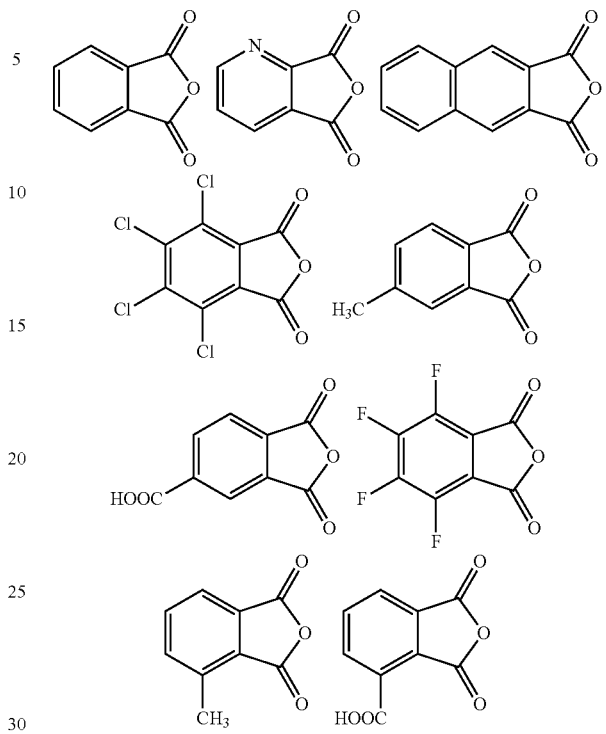

The compound represented by the general formula (5) can be obtained by mixing approximately the same amounts by mole of 8-hydroxyjulolidine and the compound represented by the general formula (4), and then refluxing the mixture in a solvent capable of dissolving the two compounds, but incapable of reacting with these compounds.

Examples of such solvent include toluene, xylene, benzene, dichloromethane and dichloroethane.

Further, it is preferred that this reaction be performed under an inert atmosphere such as a nitrogen gas atmosphere and an argon gas atmosphere.

The reaction time is 3 to 15 hours, more preferably about 5 to 12 hours. After the reaction is finished, the reaction product may be purified by, for example, silica gel chromatography.

Next, hydroquinone is mixed with the compound represented by the general formula (5). The compound represented by the general formula (5) is used in an amount of 2 to 3 equivalents, preferably about 2 equivalents based on hydroquinone, and the mixture is reacted in the presence of a condensing agent. Here, although there are no particular restrictions on such condensing agent, examples thereof may include sulfuric acid, hydrochloric acid, phosphoric acid, polyphosphoric acid, sulfonic acid, methanesulfonic acid, toluenesulfonic acid, trifluoroacetic acid, trifluoromethanesulfonic acid, aluminum trichloride, zinc chloride and phosphoryl chloride. The reaction temperature is about room temperature to 200° C., preferably room temperature to 150° C. Although the reaction time may vary depending on the reaction temperature, it is normally about 10 min to 3 days, preferably 3 to 12 hours if heated. After the reaction is finished, the reaction solution is neutralized and then purified to obtain a compound represented by the general formula (6).

Here, the compound represented by the general formula (6) includes the compound represented by the general formula (1). That is, in the abovementioned reaction, identical or different kinds of the compound represented by the general formula (5) may be employed. The compound represented by the general formula (6) can be obtained when there are employed identical kinds of the compound represented by the general formula (5); whereas the compound represented by the general formula (1) can be obtained when there are employed different kinds of the compound represented by the general formula (5).

Further, the present invention also provides a compound represented by the following general formula (2).

[Chemical formula 11]

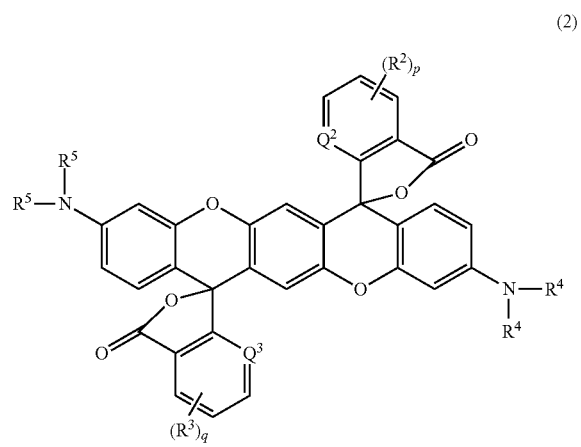

(2)

In the general formula (2), each of $Q^2$ and $Q^3$ represents $C(R)$ or N; R represents a hydrogen atom, a halogen atom, an alkyl group having 1 to 6 carbon atoms, or a carboxyl group. $R^2$ represents a halogen atom, an alkyl group having 1 to 6 carbon atoms, or a carboxyl group, where two $R^2$s may bind to each other to form a ring. $R^3$ represents a halogen atom, an alkyl group having 1 to 6 carbon atoms, or a carboxyl group, where two $R^3$s may bind to each other to form a ring. p represents a number of 1 to 3. q represents a number of 1 to 3. Each of $R^4$ and $R^5$ represents a hydrogen atom or an alkyl group having 1 to 6 carbon atoms.

Examples of the halogen atom represented by each of R, $R^2$ and $R^3$ in the general formula (2), include a fluorine atom, a chlorine atom, a bromine atom and an iodine atom. Further, the alkyl group having 1 to 6 carbon atoms, as represented by each of R, $R^2$, $R^3$, $R^4$ and $R^5$ in the general formula (2), may be either linear or branched, and examples of which may even include a cycloalkyl group and a bicycloalkyl group. Specific examples of such alkyl group include a methyl group, an ethyl group, a propyl group, an isopropyl group, an n-butyl group, an isobutyl group, an s-butyl group, a t-butyl group, a pentyl group and a hexyl group.

Further, when there are multiple Rs, $R^2$s or $R^3$s, the Rs may differ from one another, the $R^2$s may differ from one another, and the $R^3$s may differ from one another as well. As for the two $R^4$s and the two $R^5$s, the $R^4$s may be either identical to or different from each other, and the $R^5$s may be either identical to or different from each other as well.

By exchange of hydrogen ions, the compound represented by the general formula (2) may exhibit three types of structures which are a neutral form, a monocationic form and a dicationic form that are shown below.

[Chemical formulae 12]

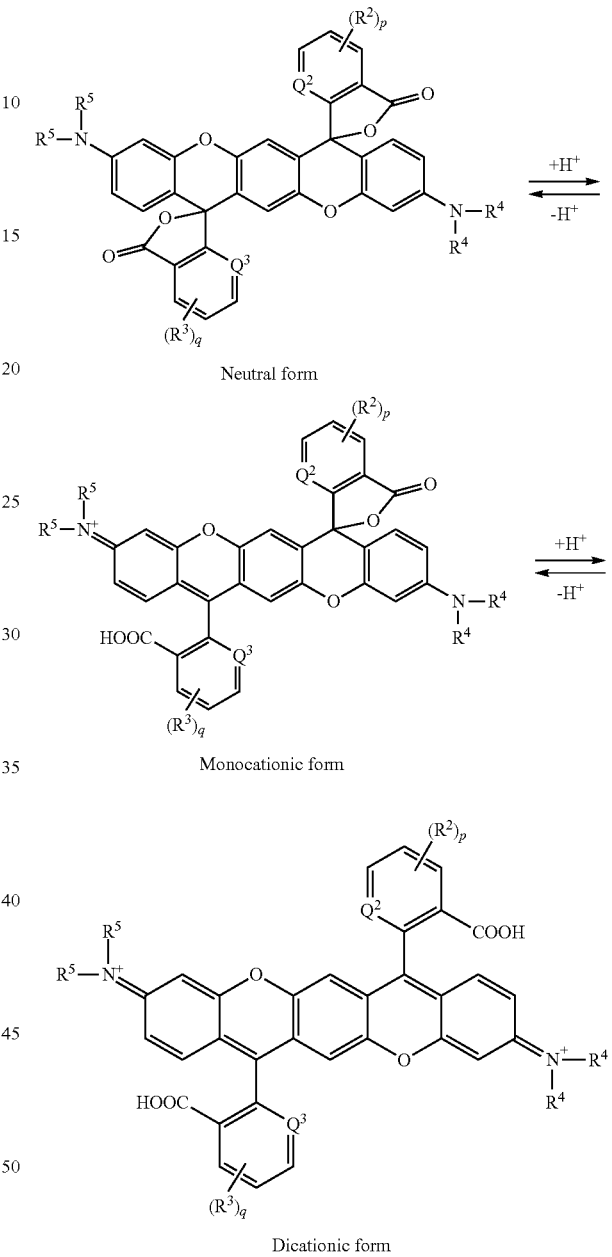

Neutral form

Monocationic form

Dicationic form

In the present invention, the compound represented by the general formula (2) includes these three types of structures.

The compound of the invention that is represented by the general formula (2) can be produced by the following method.

That is, a compound represented by a general formula (9) is obtained by reacting a compound represented by a general formula (7) with a compound represented by a general formula (8). Next, the compound represented by the general formula (9) is reacted with hydroquinone in the presence of a condensing agent.

[Chemical formula 13]

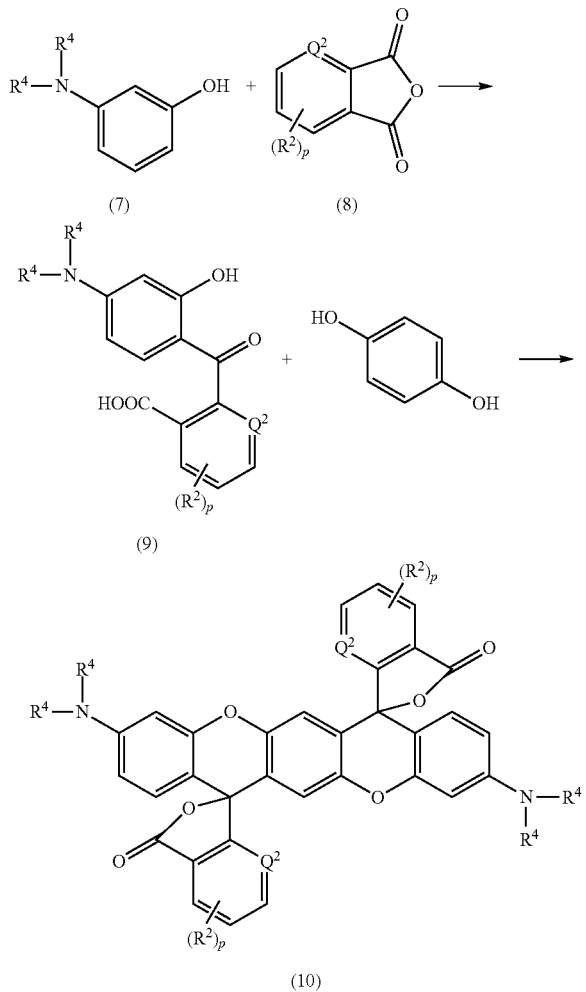

In the general formulae (7) to (10), $Q^2$ represents C(R) or N; R represents a hydrogen atom, a halogen atom, an alkyl group having 1 to 6 carbon atoms, or a carboxyl group. $R^2$ represents a halogen atom, an alkyl group having 1 to 6 carbon atoms, or a carboxyl group, where two $R^2$s may bind to each other to form a ring. p represents a number of 1 to 3. $R^4$ represents a hydrogen atom or an alkyl group having 1 to 6 carbon atoms.

Examples of the halogen atom represented by each of R and $R^2$ include a fluorine atom, a chlorine atom, a bromine atom and an iodine atom. Further, examples of the alkyl group having 1 to 6 carbon atoms, as represented by each of R, $R^2$ and $R^4$, may include groups similar to those in the general formula (2). When there are multiple Rs or $R^2$s, the Rs may be either identical to or different from one another, and the $R^2$s may be either identical to or different from one another as well.

Further, the two $R^4$s in the general formula (7) may be either identical to or different from each other. However, it is particularly preferred that the compound represented by the general formula (7) be that in which the two $R^4$s are ethyl groups or butyl groups. Examples of the compound represented by the general formula (8) include compounds similar to those listed as the examples of the compound represented by the general formula (4).

The compound represented by the general formula (9) can be obtained by mixing approximately the same amounts by mole of the compound represented by the general formula (7) and the compound represented by the general formula (8), and then refluxing the mixture in a solvent capable of dissolving the two compounds, but incapable of reacting with these compounds.

Examples of such solvent include toluene, xylene, benzene, dichloromethane and dichloroethane.

Further, it is preferred that this reaction be performed under an inert atmosphere such as a nitrogen gas atmosphere and an argon gas atmosphere.

The reaction time is 5 to 48 hours, preferably about 5 to 12 hours. After the reaction is finished, the reaction product may be purified by, for example, silica gel chromatography.

Next, hydroquinone is mixed with the compound represented by the general formula (9). The compound represented by the general formula (9) is used in an amount of 2 to 3 equivalents, preferably about 2 equivalents based on hydroquinone, and the mixture is reacted in the presence of a condensing agent. Here, although there are no particular restrictions on such condensing agent, examples thereof may include sulfuric acid, hydrochloric acid, phosphoric acid, polyphosphoric acid, sulfonic acid, methanesulfonic acid, toluenesulfonic acid, trifluoroacetic acid, trifluoromethanesulfonic acid, aluminum trichloride, zinc chloride and phosphoryl chloride.

The reaction temperature is about room temperature to 200° C., preferably room temperature to 150° C. Although the reaction time may vary depending on the reaction temperature, it is normally about 10 min to 3 days; preferably 2 to 20 hours, more preferably 3 to 12 hours, if heated. After the reaction is finished, the reaction solution is neutralized and then purified to obtain a compound represented by the general formula (10).

Here, the compound represented by the general formula (10) includes the compound represented by the general formula (2). That is, in the abovementioned reaction, identical or different kinds of the compound represented by the general formula (9) may be employed. The compound represented by the general formula (10) can be obtained when there are employed identical kinds of the compound represented by the general formula (9); whereas the compound represented by the general formula (2) can be obtained when there are employed different kinds of the compound represented by the general formula (9).

Further, the present invention also provides a compound represented by the following general formula (2').

[Chemical formula 14]

(2')

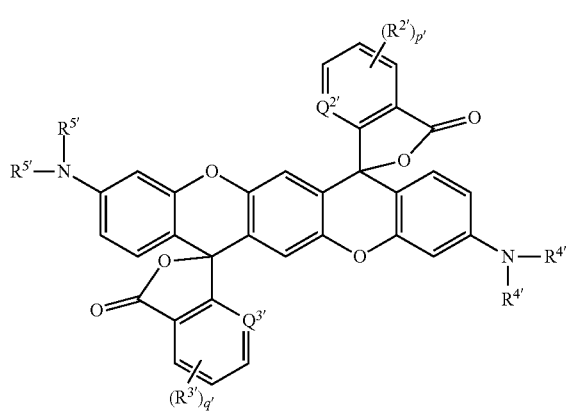

In the general formula (2'), each of $Q^{2'}$ and $Q^{3'}$ represents C(R') or N; R' represents a hydrogen atom, a halogen atom, an alkyl group having 1 to 6 carbon atoms, or a carboxyl group. $R^{2'}$ represents a hydrogen atom, a halogen atom, an alkyl group having 1 to 6 carbon atoms, or a carboxyl group, where two $R^{2'}$s may bind to each other to form a ring. $R^{3'}$ represents a hydrogen atom, a halogen atom, an alkyl group having 1 to 6 carbon atoms, or a carboxyl group, where two $R^{3'}$s may bind to each other to form a ring. p' represents a number of 0 to 3. q' represents a number of 0 to 3. Each of $R^{4'}$, and $R^{5'}$ represents a hydrogen atom or an alkyl group having 6 to 12 carbon atoms.

The alkyl group represented by each of $R^{4'}$ and $R^{5'}$ may be either linear or branched, examples of which may even include a cycloalkyl group and a bicycloalkyl group. Specific examples of such alkyl group include a hexyl group, a heptyl group, an octyl group, a nonyl group, a decyl group, an undecyl group and a dodecyl group.

Specific examples of R', $R^{2'}$ and $R^{3'}$ are similar to those listed as the specific examples of R, $R^2$ and $R^3$ in the general formula (2).

As is the case with the compound represented by the general formula (2), the compound represented by the general formula (2') may exhibit three types of structures which are a neutral form, a monocationic form and a dicationic form. In the present invention, the compound represented by the general formula (2') includes these three types of structures.

Further, the compound represented by the general formula (2') can be produced according to the method for producing the compound represented by the general formula (2).

In addition, the present invention provides a reagent for detecting phenols. This reagent contains a compound represented by a general formula (3).

[Chemical formula 15]

(3)

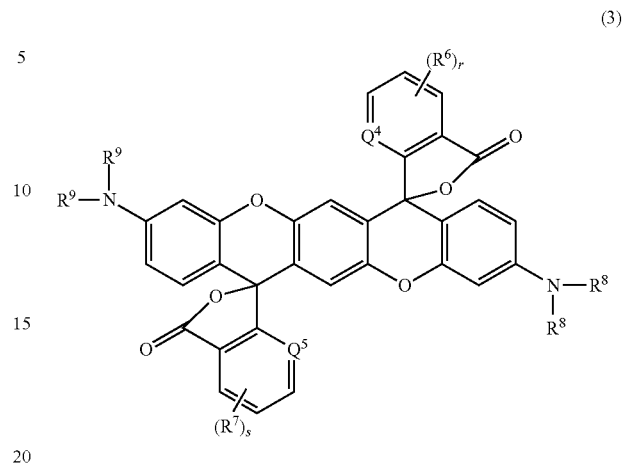

In the general formula (3), each of $Q^4$ and $Q^5$ represents C(R) or N; R represents a hydrogen atom, a halogen atom, an alkyl group having 1 to 6 carbon atoms, or a carboxyl group. $R^6$ represents a halogen atom, an alkyl group having 1 to 6 carbon atoms, or a carboxyl group, where two $R^6$s may bind to each other to form a ring. $R^7$ represents a halogen atom, an alkyl group having 1 to 6 carbon atoms, or a carboxyl group, where two $R^7$s may bind to each other to form a ring. r represents a number of 0 to 3. s represents a number of 0 to 3. Each of $R^8$ and $R^9$ may represent a hydrogen atom or an alkyl group having 1 to 6 carbon atoms; or $R^8$s or $R^9$s may form a julolidine structure together with a nitrogen atom bonded thereto and a benzene ring adjacent to such nitrogen atom.

Phenols refer to compounds consisting of hydroxy group(s) bonded to aromatic substituents, and specific examples of such phenols include the following compounds.
Monovalent phenol: phenol, cresol, naphthol
Divalent phenol: catechol, resorcinol, hydroquinone
Trivalent phenol: pyrogallol, phloroglucinol When the compound represented by the general formula (3) and phenols have come into contact with each other, the lactone ring(s) of the compound represented by the general formula (3) will open such that the structure of the compound will be converted to that having a different absorption wavelength. Since the structure of the compound of the invention that is represented by the general formula (3) changes in two stages depending on the concentration of phenols, such compound is useful as a reagent for detecting phenols of multiple stages.

WORKING EXAMPLE

The invention of the present application is described in greater detail hereunder with reference to working and comparative examples. However, the invention of the present application shall not be limited to the following examples.
$^1$H-NMR measurement was performed using JNM-AL400 (by JEOL Ltd.) or JNM-AL300 (JEOL Ltd.)
Absorption spectrum was measured using JASCO V-670 (by JASCO Corporation).
Fluorescence spectrum was measured using JASCO FP-6600 (by JASCO Corporation).
MS spectrum was measured using micrOTOF-QIII (by Bruker Daltonics) or Ultraflex (Bruker Daltonics).

Working Example 1

Added to sulfuric acid (3 mL) was a mixture of 9-(2-carboxybenzoyl)-8-hydroxyjulolidine (compound (5-1), 3.00 mmol, synthesized by a method described in document: Kamino et al., Org. Lett., 2014, 16, 258.) and hydroquinone (1.50 mmol, purchased from Tokyo Chemical Industry Co., Ltd.), followed by stirring them at room temperature for two days, neutralizing the reaction solution with an aqueous sodium hydroxide solution, and then collecting an insoluble(s) by filtration. The insoluble(s) was then dissolved in chloroform, followed by performing purification through silica gel chromatography to obtain compounds (6-1-1) and (6-1-2) as faint pink solids. At that time, the compound (6-1-1) flew out first, and the compound (6-1-2) flew out later. A yield was 8% with (6-1-1) and (6-1-2) combined. The reaction formula is shown below.

[Chemical formula 16]

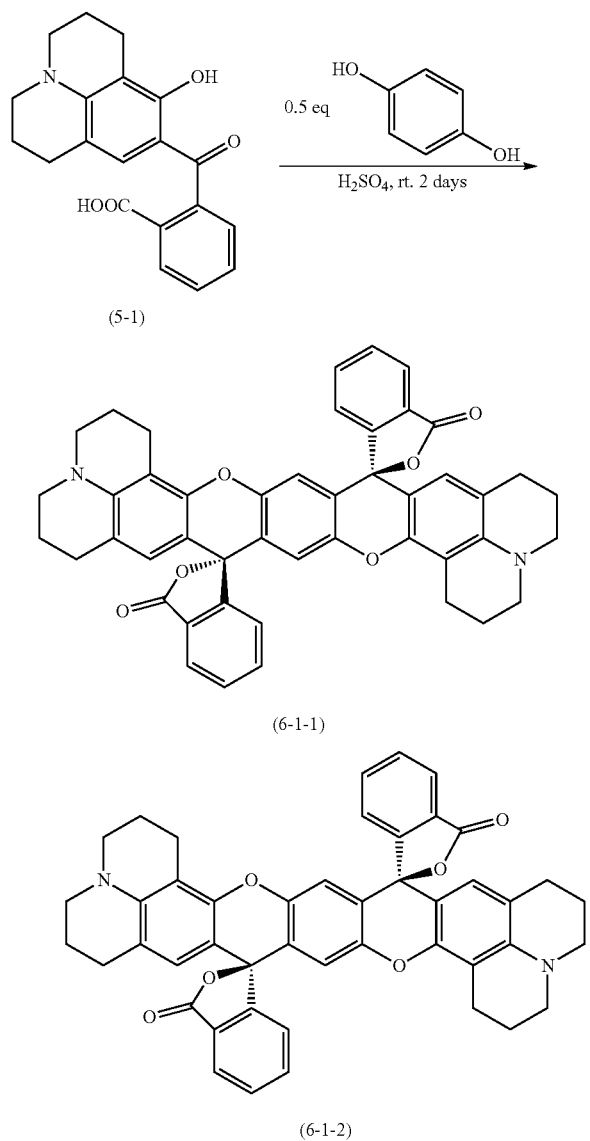

Data of Compound (6-1-1):

400 MHz $^1$H-NMR (CDCl$_3$/TMS) δ (ppm): 8.06 (2H, d), 7.69 (4H, m), 7.24 (2H, d), 6.64 (2H, s), 6.12 (2H, s), 3.13 (8H, m), 2.80 (4H, m), 2.52 (4H, m), 1.97 (4H, m), 1.86 (4H, m).

IR (ATR, cm$^{-1}$): 1748, 1620, 1423, 1309, 1192, 1096, 862.

UV/Vis: $\lambda_{max}$=676 nm (dicationic form, 10 vol % CF$_3$COOH/CHCl$_3$).

HRMS (ESI) m/z calcd. for C$_{46}$H$_{37}$N$_2$O$_6$ ([M+H]$^+$): 713.2646, found: 713.2691.

Data of Compound (6-1-2):

400 MHz $^1$H-NMR (CDCl$_3$/TMS) δ (ppm): 8.05 (2H, d), 7.64 (4H, m), 7.16 (2H, d), 6.70 (2H, s), 6.15 (2H, s), 3.11 (8H, m), 2.80 (4H, m), 2.51 (4H, m), 1.95 (4H, m), 1.85 (4H, m).

IR (ATR, cm$^{-1}$): 1749, 1621, 1425, 1310, 1192, 1097, 861.

UV/Vis: $\lambda_{max}$=676 nm (dicationic form, 10 vol % CF$_3$COOH/CHCl$_3$).

HRMS (ESI) m/z calcd. for C$_{46}$H$_{37}$N$_2$O$_6$ ([M+H]$^+$): 713.2646, found: 713.2690.

The compounds obtained in working example 1 were dissolved in chloroform, and the absorption spectrum thereof was measured (neutral form). Next, trifluoroacetic acid was added to this solution of the neutral form so that trifluoroacetic acid would be present at 0.01 vol %, followed by measuring the absorption spectrum thereof in a similar manner (monocationic form). Trifluoroacetic acid was further added to this solution of the monocationic form so that trifluoroacetic acid would be present at 0.2 vol %, followed by measuring the absorption spectrum thereof in a similar manner as well (dicationic form).

The absorption spectrum of each structure is shown in FIG. 1.

While a colorless solution was observed when the compound was in the neutral form, a pink solution was observed when the compound was in the monocationic form, and a blue-green solution was observed when the compound was in the dicationic form i.e. the solution of the monocationic form and the solution of the dicationic form differed from each other in hue.

Figure 2:
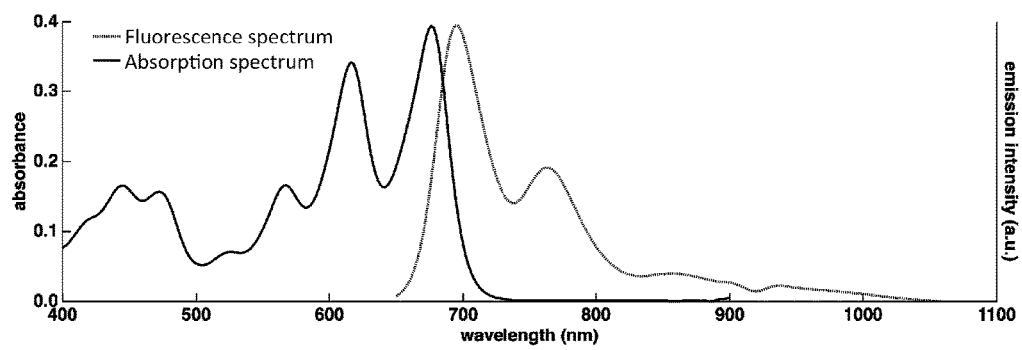
FIG. 2 is a diagram showing the absorption and fluorescence spectra of the compound (in dicationic form) obtained in working example 1.

Next, fluorescence spectrum measurement was performed using a 10 vol % trifluoroacetic acid/chloroform solution of the compounds obtained in working example 1 (dicationic form). The results thereof are shown in FIG. 2.

A 0.2 vol % trifluoroacetic acid/chloroform solution of the compounds obtained in working example 1 was prepared so that the concentration of the compounds was 0.04 mmol/L, and the absorption spectrum of the solution was then measured.

Comparative Example 1

Absorption spectrum measurement was performed under similar conditions except that the following compound synthesized according to a publication (specification of U.S. Pat. No. 3,663,571) was employed instead of the compounds obtained in working example 1.

[Chemical formula 17]

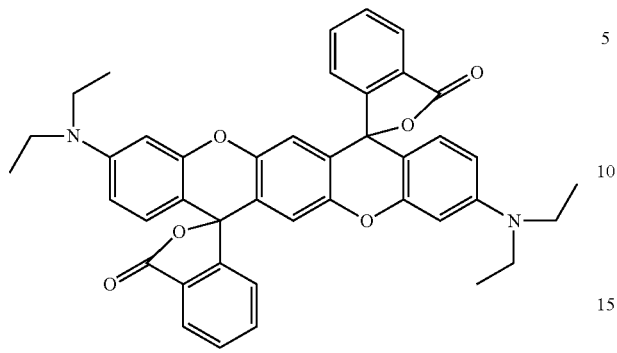

Table 1 summarizes the measurement results of absorbance at the wavelength of maximum absorption in each of working example 1 and comparative example 1. As shown in Table 1, it became clear that at the same concentration of the acid, the compound(s) of working example 1 exhibited a sensitivity about 160 times higher than that of the compound of comparative example 1.

TABLE 1

|  | Absorbance |
| --- | --- |
| Working example 1 | 0.254 (676 nm) |
| Comparative example 1 | 0.00159 (660 nm) |

Working Example 2

Under a nitrogen atmosphere, added to toluene (10 mL) was a mixture of 8-hydroxyjulolidine (3.00 mmol, purchased from Wako Pure Chemical Industries, Ltd.) and 3,4,5,6-tetrafluorophthalic anhydride (compound (4-2), 3.00 mmol, purchased from Wako Pure Chemical Industries, Ltd.), followed by heating and refluxing them for five hours while performing stirring. After the reaction solution was cooled to room temperature, hexane was added thereto to collect an insoluble(s) by filtration. The insoluble(s) was dissolved in chloroform, and then purified by silica gel chromatography to obtain a compound (5-2) as a faint green solid. A yield was 63%. The reaction formula is shown below.

[Chemical formula 18]

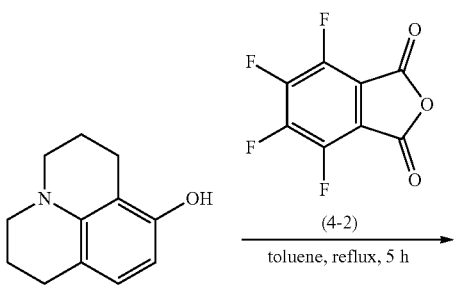

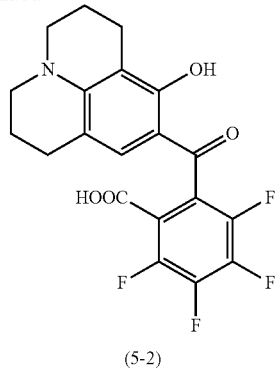

(5-2)

Data of Compound (5-2):
400 MHz $^1$H-NMR (CDCl$_3$/TMS) δ (ppm): 12.28 (1H, s), 6.49 (1H, s), 3.28 (4H, t), 2.71 (2H, t), 2.55 (2H, t), 1.92 (4H, m).
HRMS (ESI) m/z calcd. for C$_{20}$H$_{14}$F$_4$NO$_4$ ([M−H]$^-$): 408.0864, found: 408.0884.

Added to sulfuric acid (0.3 mL) was a mixture of 9-(2-carboxy-3,4,5,6-tetrafluorobenzoyl)-8-hydroxyjulolidine (compound (5-2), 0.22 mmol) and hydroquinone (0.10 mmol, purchased from Tokyo Chemical Industry Co., Ltd.), followed by stirring them at 135° C. for four hours. The reaction solution was then neutralized with an aqueous sodium hydroxide solution, and an insoluble(s) was later collected by filtration. The insoluble(s) was dissolved in chloroform, and then purified by silica gel chromatography to obtain a compound (6-2) as a colorless solid. A yield was 2%. The reaction formula is shown below.

[Chemical formula 19]

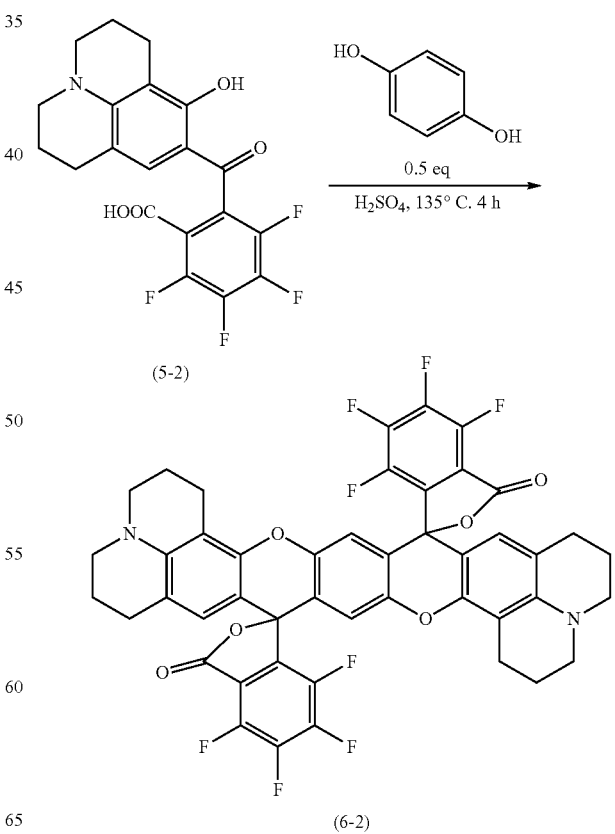

Data of Compound (6-2):

UV/Vis: $\lambda_{max}$=688 nm (dicationic form, 10 vol % $CF_3COOH/CHCl_3$).

HRMS (ESI) m/z calcd. for $C_{46}H_{29}F_8N_2O_6$ ([M+H]$^+$): 857.1892, found: 857.1896.

The compounds obtained in working example 2 were dissolved in chloroform, and the absorption spectrum thereof was measured (neutral form). Next, trifluoroacetic acid was added to this solution of the neutral form so that trifluoroacetic acid would be present at 0.01 vol %, followed by measuring the absorption spectrum thereof in a similar manner (monocationic form). Trifluoroacetic acid was further added to this solution of the monocationic form so that trifluoroacetic acid would be present at 2 vol %, followed by measuring the absorption spectrum thereof in a similar manner as well (dicationic form).

Figure 3:
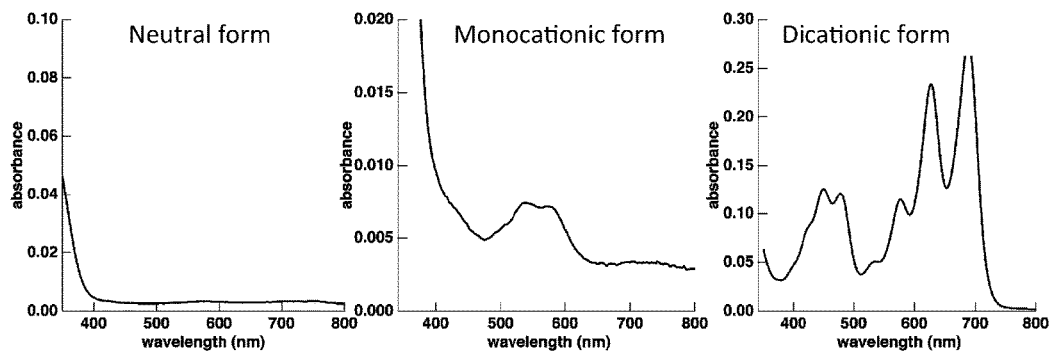
FIG. 3 is a diagram showing the absorption spectra of a compound obtained in working example 2.

The absorption spectrum of each structure is shown in FIG. 3.

While a colorless solution was observed when the compound was in the neutral form, a pink solution was observed when the compound was in the monocationic form, and a blue-green solution was observed when the compound was in the dicationic form i.e. the solution of the monocationic form and the solution of the dicationic form differed from each other in hue.

Figure 4:
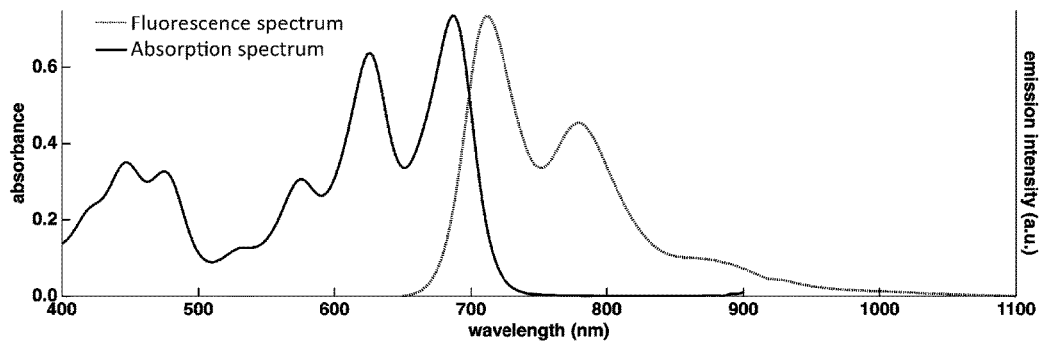
FIG. 4 is a diagram showing the absorption and fluorescence spectra of the compound (in dicationic form) obtained in working example 2.

Measured were the absorption spectrum and fluorescence spectrum of the compounds obtained in working example 2, in 10 vol % trifluoroacetic acid/chloroform. The results thereof are shown in FIG. 4.

Working Example 3

Under a nitrogen atmosphere, added to toluene (10 mL) was a mixture of 8-hydroxyjulolidine (2.00 mmol, purchased from Wako Pure Chemical Industries, Ltd.) and 4-methylphthalic anhydride (compound (4-3), 3.00 mmol, purchased from Tokyo Chemical Industry Co., Ltd.), followed by heating and refluxing them for 12 hours while performing stirring. After the reaction solution was cooled to room temperature, hexane was added thereto to collect an insoluble(s) by filtration. The insoluble(s) was dissolved in chloroform, and then purified by silica gel chromatography to obtain a compound (5-3) as a brown solid. A yield was 34%. The reaction formula is shown below.

[Chemical formula 20]

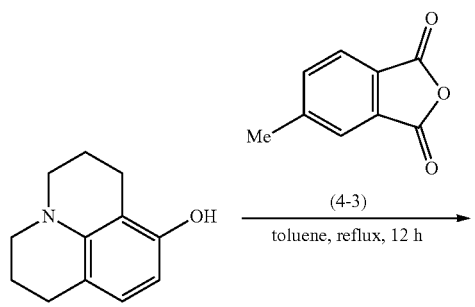

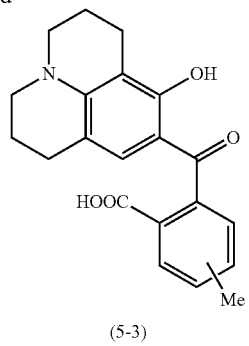

(5-3)

Data of Compound (5-3):

HRMS (ESI) m/z calcd. for $C_{21}H_{20}NO_4$ ([M–H]$^-$): 350.1397, found: 350.1398.

Added to sulfuric acid (3 mL) were a mixture (compound (5-3), 0.5 mmol) of 9-(2-carboxy-4-methylbenzoyl)-8-hydroxyjulolidine and 9-(2-carboxy-5-methylbenzoyl)-8-hydroxyjulolidine; and hydroquinone (0.25 mmol, purchased from Tokyo Chemical Industry Co., Ltd.), followed by stirring them at room temperature for three days. The reaction solution was then neutralized with an aqueous sodium hydroxide solution, and an insoluble(s) was later collected by filtration. The insoluble(s) was dissolved in chloroform, and then purified by silica gel chromatography to obtain a compound (6-3) as a faint pink solid. A yield was 3%. The reaction formula is shown below.

[Chemical formula 21]

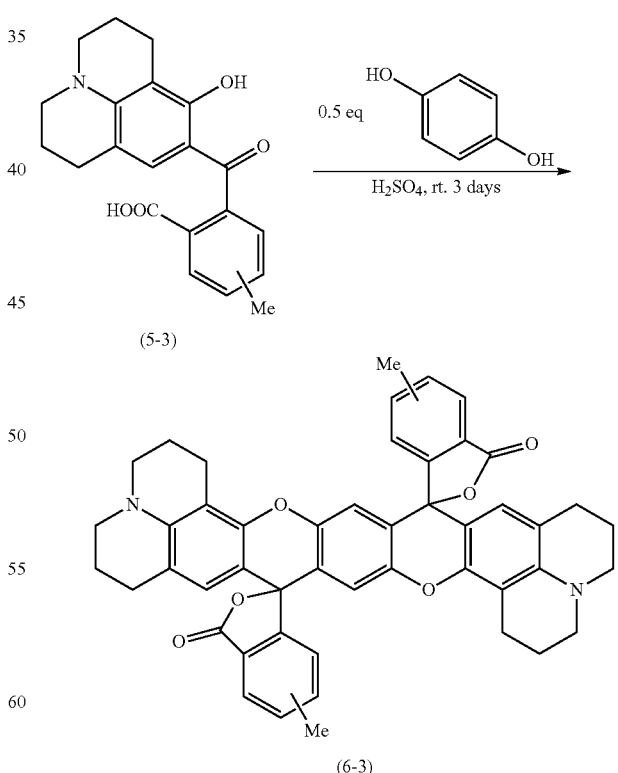

Data of Compound (6-3):

UV/Vis: $\lambda_{max}$=675 nm (dicationic form, 10 vol % $CF_3COOH/CHCl_3$).

HRMS (ESI) m/z calcd. for $C_{48}H_{41}N_2O_6$ ([M+H]$^+$): 741.2959, found: 741.3003.

Working Example 4

Under a nitrogen atmosphere, added to toluene (10 mL) was a mixture of 8-hydroxyjulolidine (3.00 mmol, purchased from Wako Pure Chemical Industries, Ltd.) and 3,4,5,6-tetrachlorophthalic anhydride (compound (4-4), 3.61 mmol, purchased from Wako Pure Chemical Industries, Ltd.), followed by heating and refluxing them for three hours while performing stirring. After the reaction solution was cooled to room temperature, hexane was added thereto to collect an insoluble(s) by filtration. The insoluble(s) was dissolved in chloroform, and then purified by silica gel chromatography to obtain a compound (5-4) as a yellow solid. A yield was 40%. The reaction formula is shown below.

[Chemical formula 22]

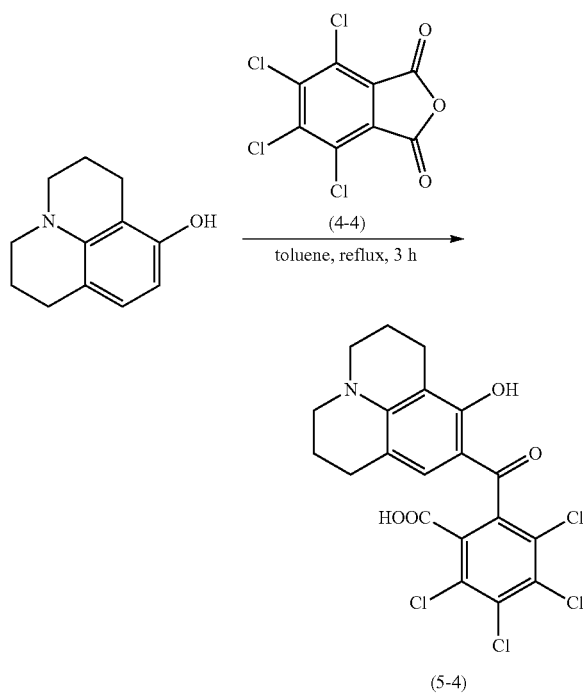

[Chemical formula 23]

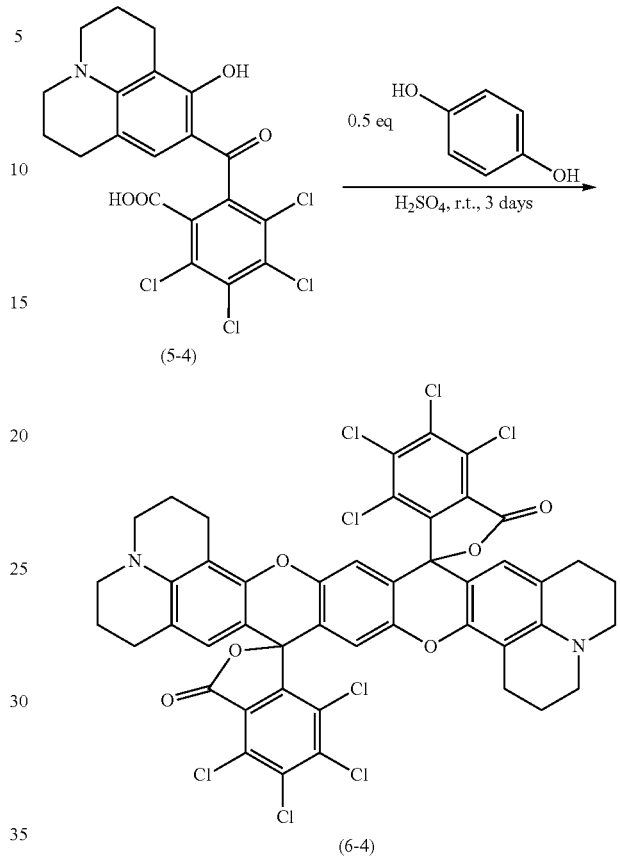

Data of Compound (5-4):

500 MHz $^1$H-NMR (CDCl$_3$/TMS) δ (ppm): 12.33 (1H, s), 6.46 (1H, s), 3.28 (4H, t), 2.69 (2H, t), 2.54 (2H, t), 1.91 (4H, m).

Added to sulfuric acid (1.5 mL) was a mixture of 9-(2-carboxy-3,4,5,6-tetrachlorobenzoyl)-8-hydroxyjulolidine (compound (5-4), 1.0 mmol) and hydroquinone (0.50 mmol, purchased from Tokyo Chemical Industry Co., Ltd.), followed by stirring them at room temperature for three days. The reaction solution was then neutralized with an aqueous potassium carbonate solution, and an insoluble(s) was later collected by filtration. The insoluble(s) was dissolved in chloroform, and then purified by silica gel chromatography to obtain a compound (6-4) as a colorless solid. A yield was 5%. The reaction formula is shown below.

Data of Compound (6-4):

UV/Vis: $\lambda_{max}$=687 nm (dicationic form, 5 vol % CH$_3$SO$_3$H/MeOH).

MS (MALDI) m/z calcd. for $C_{46}H_{28}Cl_{18}N_2O_6$ ([M]$^+$): 987.9397, found: 988.

Working Example 5

Added to sulfuric acid (1.84 mL) were a mixture of 2-(4-diethylamino-2-hydroxybenzoyl)-4-methyl-benzoic acid and 2-(4-diethylamino-2-hydroxybenzoyl)-5-methyl-benzoic acid (compound (9-5), 0.562 mmol, synthesized by a method described in document: WO2014/002292); and hydroquinone (0.280 mmol, purchased from Tokyo Chemical Industry Co., Ltd.), followed by stirring them at 110° C. for 4.5 hours. The reaction solution was then neutralized with an aqueous sodium hydroxide solution, and an insoluble(s) was later collected by filtration. The insoluble(s) was dissolved in chloroform, and then purified by silica gel chromatography to obtain a compound (10-5) as a faint blue solid. A yield was 7%. The reaction formula is shown below.

[Chemical formula 24]

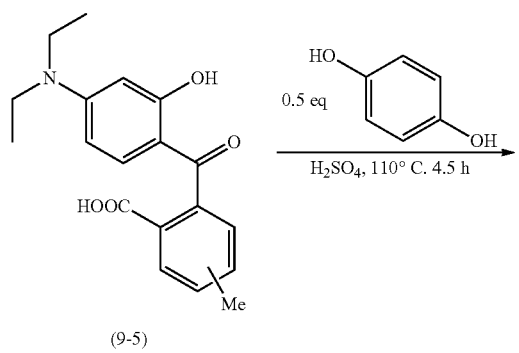

(9-5)

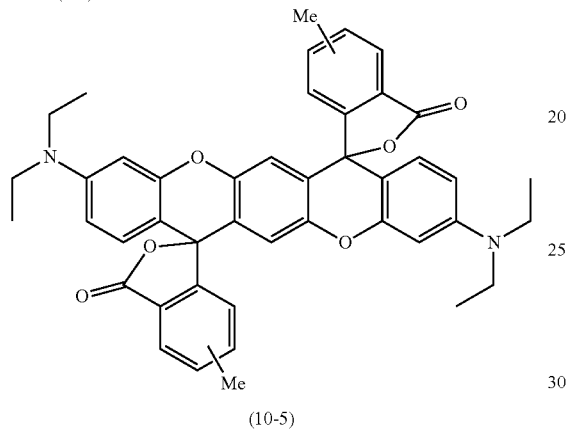

(10-5)

Data of Compound (10-5):

UV/Vis: $\lambda_{max}$=659 nm (dicationic form, 10 vol % $CF_3COOH/CHCl_3$).

HRMS (ESI) m/z calcd. for $C_{46}H_{37}N_2O_6$ ([M+H]$^+$): 693.2959, found: 693.2978.

Working Example 6

Under a nitrogen atmosphere, added to toluene (2.4 mL) was a mixture of N,N-dibutyl-m-aminophenol (compound (7-6), 3.0 mmol, purchased from Wako Pure Chemical Industries, Ltd.) and 4-methylphthalic anhydride (compound (8-6), 3.0 mmol, purchased from Wako Pure Chemical Industries, Ltd.), followed by heating and refluxing them for 22 hours while performing stirring. After the reaction solution was cooled to room temperature, an aqueous sodium hydroxide solution and chloroform were added to the reaction solution to perform liquid-liquid extraction. After acidizing a separated aqueous layer with hydrochloric acid, extraction was later performed with chloroform. After drying an organic layer with anhydrous sodium sulfate, chloroform was distilled away under a reduced pressure to obtain a red solid crude product. By performing purification via silica gel chromatography, a compound (9-6) was obtained as a dark red candy-like substance. A yield was 18%. The reaction formula is shown below.

[Chemical formula 25]

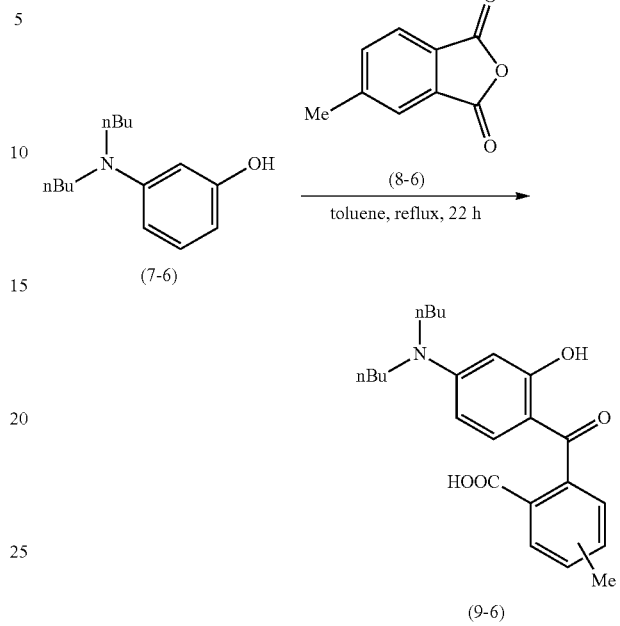

(9-6)

Data of Compound (9-6):

HRMS (ESI) m/z calcd. for $C_{23}H_{28}NO_4$ ([M−H]$^-$): 382.2018, found: 382.2048.

Added to methanesulfonic acid (0.35 mL) were a mixture ((9-6), 0.106 mmol) of 2-(4-(dibutylamino)-2-hydroxybenzoyl)-4-methyl benzoic acid and 2-(4-(dibutylamino)-2-hydroxybenzoyl)-5-methyl benzoic acid; and hydroquinone (0.053 mmol, purchased from Tokyo Chemical Industry Co., Ltd.), followed by stirring them at 110° C. for 19 hours. The reaction solution was then neutralized with an aqueous sodium hydroxide solution, and later extracted with chloroform. After drying an organic layer with anhydrous sodium sulfate, the solvent was distilled away under a reduced pressure to obtain a dark brown candy-like crude product. Purification was performed via silica gel chromatography, and then size exclusion chromatography, to obtain a compound (10-6) as a brown solid. A yield was 8%. The reaction formula is shown below.

[Chemical formula 26]

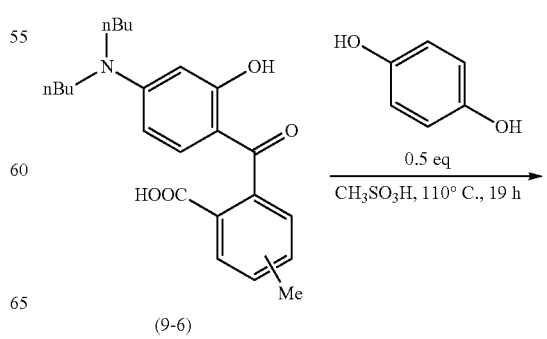

(9-6)

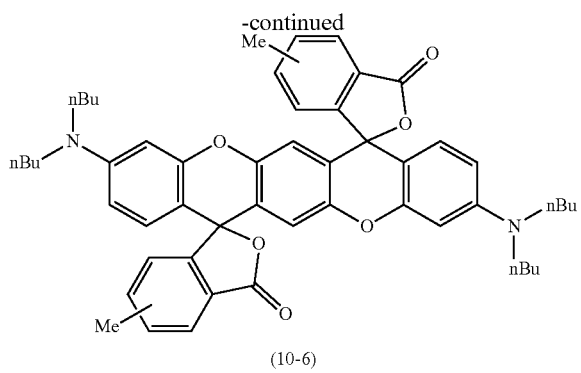

(10-6)

Data of Compound (10-6):

UV/Vis: $\lambda_{max}$=666 nm (dicationic form, $CH_3SO_3H$/$CHCl_3$).

MS (MALDI) m/z calcd. for $C_{52}H_{58}N_2O_6$ ([M+2H]$^+$): 806.4295, found: 806.

Working Example 7

Under a nitrogen atmosphere, added to toluene (20 mL) was a mixture of N,N-diethyl-m-aminophenol (compound (7-7), 10.0 mmol, purchased from Wako Pure Chemical Industries, Ltd.) and 4-tert-butylphthalic anhydride (compound (8-7), 10.0 mmol, purchased from Tokyo Chemical Industry Co., Ltd.), followed by heating and refluxing them for 48 hours while performing stirring. After the reaction solution was cooled to room temperature, toluene was distilled away under a reduced pressure to obtain a purple solid crude product. Purification was then performed via silica gel chromatography to obtain a compound (9-7) as a yellow solid. A yield was 23%. The reaction formula is shown below.

[Chemical formula 27]

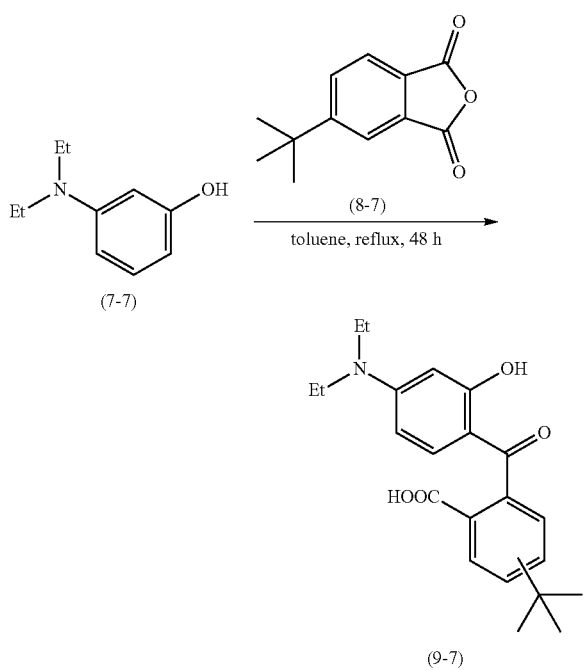

Data of Compound (9-7):

MS (ESI) m/z calcd. for $C_{22}H_{26}NO_4$ ([M−H]$^−$): 368.1862, found: 368.

Added to methanesulfonic acid (1.00 mL) were a mixture (compound (9-7), 0.5 mmol) of 2-(4-(diethylamino)-2-hydroxybenzoyl)-4-tert-butyl benzoic acid and 2-(4-(diethylamino)-2-hydroxybenzoyl)-5-tert-butyl benzoic acid; and hydroquinone (0.25 mmol, purchased from Tokyo Chemical Industry Co., Ltd.), followed by stirring them at room temperature for 24 hours, and then at 110° C. for another three hours. The reaction solution was then neutralized with an aqueous sodium hydroxide solution, and later extracted with chloroform. After drying an organic layer with anhydrous sodium sulfate, the solvent was distilled away under a reduced pressure to obtain a purple candy-like crude product. Purification was performed via silica gel chromatography, and then size exclusion chromatography, to obtain a compound (10-7) as a colorless solid. A yield was 21%. The reaction formula is shown below.

[Chemical formula 28]

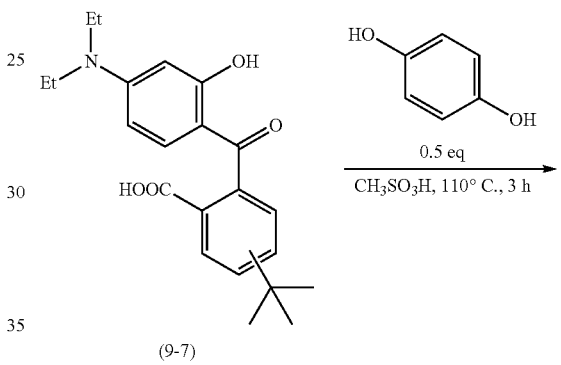

(10-7)

Data of Compound (10-7):

UV/Vis: $\lambda_{max}$=659 nm (dicationic form, 10 vol % $CF_3COOH$/$CHCl_3$).

HRMS (ESI) m/z calcd. for $C_{50}H_{53}N_2O_6$ ([M+H]$^+$): 777.3904, found: 777. 3902.

Working Example 8

Under a nitrogen atmosphere, added to toluene (4.0 mL) was a mixture of N,N-dibutyl-m-aminophenol (compound (7-8), 4.0 mmol, purchased from Tokyo Chemical Industry Co., Ltd.) and 4-bromophthalic anhydride (compound (8-8), 4.8 mmol, purchased from Wako Pure Chemical Industries, Ltd.), followed by heating and refluxing them for 12 hours while performing stirring. After the reaction solution was cooled to room temperature, toluene was distilled away under a reduced pressure to obtain a red oily crude product. Purification was then performed via silica gel chromatography to obtain a compound (9-8) as a yellow foamy substance. A yield was 26%. The reaction formula is shown below.

[Chemical formula 29]

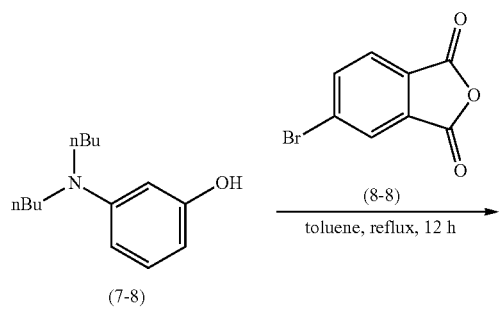

(7-8)    (8-8)
toluene, reflux, 12 h

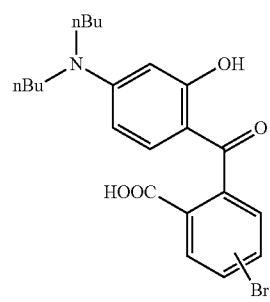

(9-8)

Data of Compound (9-8):

HRMS (ESI) m/z calcd. for $C_{22}H_{25}BrNO_4$ ([M−H]$^−$): 446.0967, found: 446. 0966.

Added to sulfuric acid (2.00 mL) were a mixture (compound (9-8), 1.04 mmol) of 2-(4-(dibutylamino)-2-hydroxybenzoyl)-4-bromobenzoic acid and 2-(4-(dibutylamino)-2-hydroxybenzoyl)-5-bromobenzoic acid; and hydroquinone (0.50 mmol, purchased from Tokyo Chemical Industry Co., Ltd.), followed by stirring them at 110° C. for two hours. The reaction solution was then neutralized with an aqueous sodium hydroxide solution, and later extracted with chloroform. After drying an organic layer with anhydrous sodium sulfate, the solvent was distilled away under a reduced pressure to obtain a purple solid crude product. Purification was performed via silica gel chromatography, and then size exclusion chromatography, to obtain a compound (10-8) as a colorless solid. A yield was 14%. The reaction formula is shown below.

[Chemical formula 30]

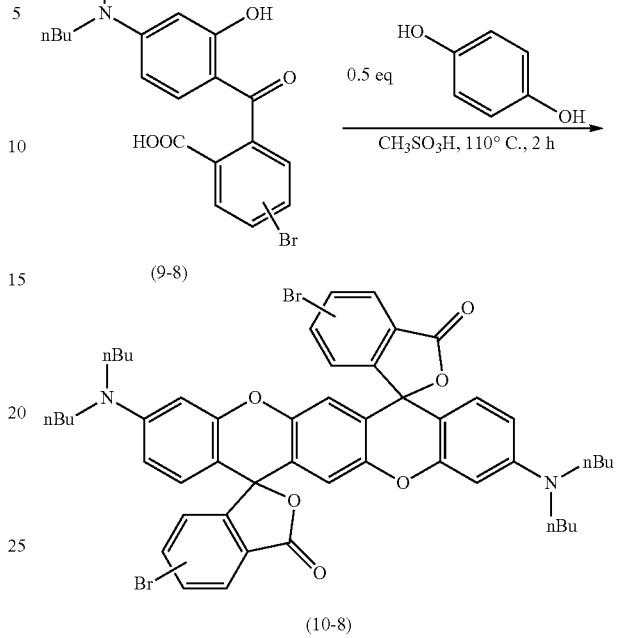

Data of Compound (10-8):

UV/Vis: $\lambda_{max}$=669 nm (dicationic form, 10 vol % $CF_3COOH/CHCl_3$).

MS (MALDI) m/z calcd. for $C_{50}H_{52}Br_2N_2O_6$ ([M+2H]$^+$): 936.2192, found: 936.

Working Example 9

Under a nitrogen atmosphere, added to toluene (2.6 mL) was a mixture of N,N-dihexyl-m-aminophenol (compound (7-9), 2.6 mmol) and phthalic anhydride (compound (8-9), 2.6 mmol, purchased from Wako Pure Chemical Industries, Ltd.), followed by heating and refluxing them for 19 hours while performing stirring. After the reaction solution was cooled to room temperature, the solvent was distilled away under a reduced pressure to obtain a red-purple candy-like crude product. Purification was then performed via silica gel chromatography to obtain a compound (9-9) as a green-brown candy-like substance. A yield was 90%. The reaction formula is shown below.

[Chemical formula 31]

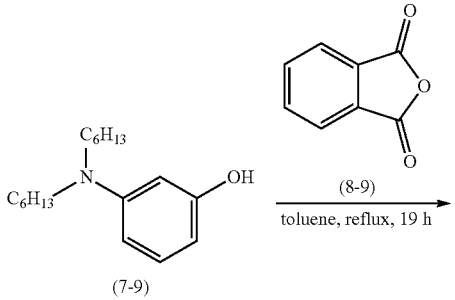

(7-9)    (8-9)
toluene, reflux, 19 h

-continued

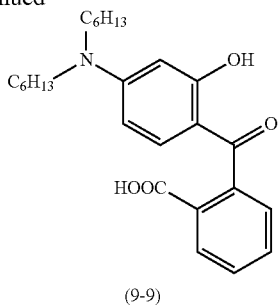

(9-9)

Data of Compound (9-9):

400 MHz $^1$H-NMR (CDCl$_3$/TMS) δ (ppm): 12.55 (1H, s), 8.11 (1H, d, J=7.5 Hz), 7.62 (1H, m), 7.54 (1H, m), 7.37 (1H, d, J=7.5 Hz), 6.88 (1H, d, J=9.0 Hz), 6.11 (1H, d, J=2.1 Hz), 6.02 (1H, dd, J=9.0, 2.4 Hz), 3.28 (4H, t, J=7.9 Hz), 1.59 (4H, bs), 1.30 (12H, m), 0.89 (6H, t, J=6.6 Hz).

MS (MALDI) m/z calcd. for $C_{26}H_{34}NO_4$ ([M−H]$^-$): 424.2488, Found 424.2.

Added to methanesulfonic acid (17 mL) was a mixture of 2-(4-(dihexylamine)-2-hydroxybenzoyl benzoic acid (compound (9-9), 9.02 mmol) and hydroquinone (4.56 mmol, purchased from Wako Pure Chemical Industries, Ltd.), followed by stirring them at 100° C. for four hours. The reaction solution was then neutralized with an aqueous sodium hydroxide solution, and later extracted with chloroform. After drying an organic layer with anhydrous sodium sulfate, the solvent was distilled away under a reduced pressure to obtain a black-green candy-like crude product. Purification was performed via silica gel chromatography, and then size exclusion chromatography, to obtain a compound (10-9) as a faint red solid. A yield was 15%. The reaction formula is shown below.

[Chemical formula 32]

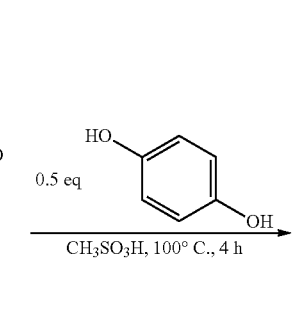

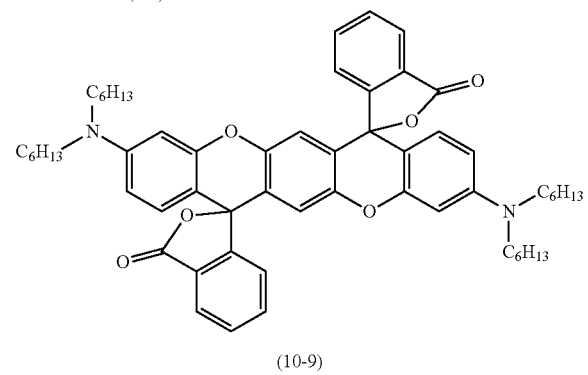

(10-9)

Data of Compound (10-9):

UV/Vis: $λ_{max}$=669 nm (dicationic form, 10 vol % CF$_3$COOH/CHCl$_3$).

MS (MALDI) m/z calcd. for $C_{58}H_{70}N_2O_6$ ([M+2]$^+$): 890.5234, Found: 890.7.

Working Example 10

As a result of thoroughly mixing 5.0 mg of the compound obtained in working example 1 and 0.03 mg of catechol in a mortar, the mixture exhibited a red-pink color. After adding 0.12 mg of catechol to this mixture, the mixture exhibited a purple color. As a result of further adding 1.3 mg of catechol to this mixture, the mixture exhibited a green color.

It became clear that the compound of the invention exhibited different colors in the solid state, depending on a weight ratio thereof to phenols.

Working Example 11

Figure 5:
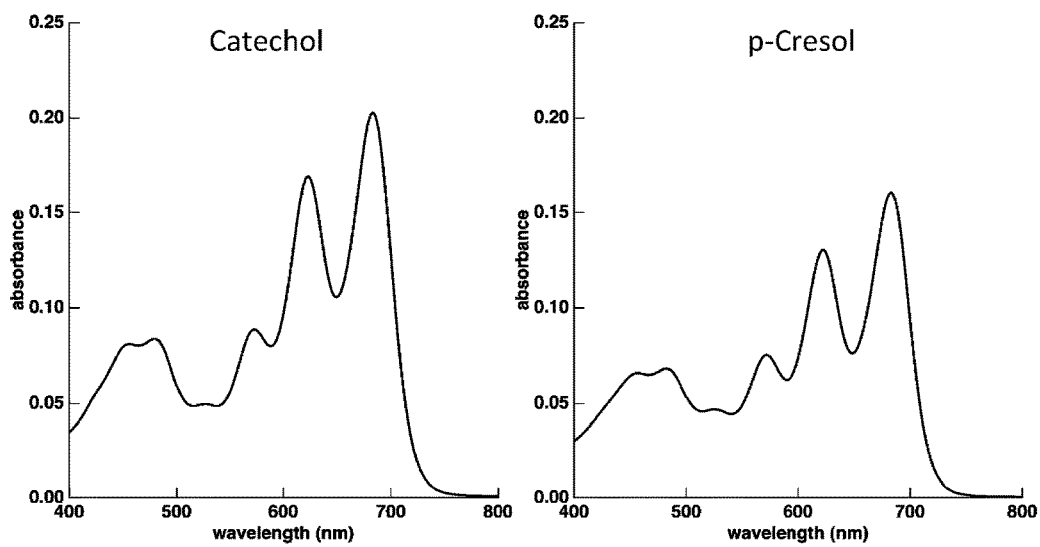
FIG. 5 is a diagram showing the absorption spectra of the compound that is obtained in working example 1, but has been reacted with phenols.

The compound obtained in working example 1 was dissolved in chloroform so that the compound would be present at 0.2 mg/L, and catechol was then added to this solution so that it would be present at 0.3 mol/L. As a result, the solution exhibited a green color. Similarly, as a result of adding p-cresol so that it would be present at 1.0 mol/L, the solution also exhibited a green color. The absorption spectrum of each solution is shown in FIG. 5.

It became clear that the compound of the invention exhibited colors in response to phenols even in the solution state.

Reference Example 1

The following compound (5-1') was obtained in a manner similar to working example 2, except that 2,3-naphthalene dicarboxylic anhydride was employed instead of 3,4,5,6-tetrafluorophthalic anhydride.

[Chemical formula 33]

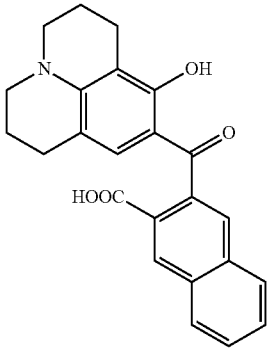

5-1'

Data of Compound (5-1'):

300 MHz $^1$H-NMR ((CD$_3$)$_2$CO/TMS) δ (ppm): 13.01 (1H, s), 8.64 (1H, s), 8.15 (1H, m), 8.04 (1H, m), 7.88 (1H, s), 7.70 (2H, m), 6.66 (1H, s), 3.28 (4H, t), 2.66 (2H, t), 2.43 (2H, t), 1.86 (4H, m).

HRMS (ESI) m/z calcd. for $C_{24}H_{20}NO_4$ ([M−H]$^-$): 386.1398, found: 386. 1394.

Reference Example 2

The following compound (5-2') was obtained in a manner similar to working example 2, except that 2,3-pyridine dicarboxylic anhydride was employed instead of 3,4,5,6-tetrafluorophthalic anhydride.

[Chemical formula 34]

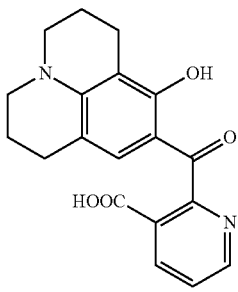

5-2'

Data of Compound (5-2'):
HRMS (ESI) m/z calcd. for $C_{19}H_{17}N_2O_4$ ([M−H]$^-$): 337.1194, found: 337. 1186.

Reference Example 3

The following compound (5-3') was obtained in a manner similar to working example 2, except that trimellitic anhydride was employed instead of 3,4,5,6-tetrafluorophthalic anhydride.

[Chemical formula 35]

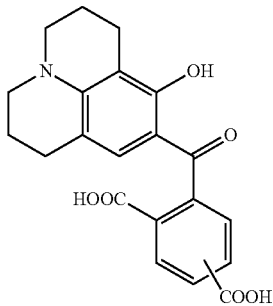

5-3'

Data of Compound (5-3'):
HRMS (ESI) m/z calcd. for $C_{21}H_{18}NO_6$ ([M−H]$^-$): 380.1140, found: 380. 1126.

By reacting any of the compounds (5-1') to (5-3') obtained in the reference examples 1 to 3 with hydroquinone, there can be obtained the compound of the present invention.

INDUSTRIAL APPLICABILITY

It is expected that the compound of the present invention, as a compound capable of exhibiting different changes in hue with one kind of molecule, may be useful in various fields such as coloring materials including colorants and dyes; indicators and diagnostic agents for compounds, including reagents for detecting phenols; coloring matters for fluorescence imaging; and dye-sensitized solar cells.

The invention claimed is:
1. A compound represented by a general formula (1):

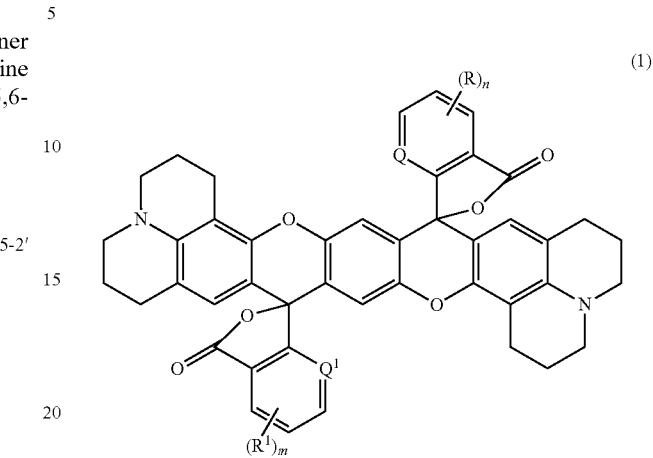

(1)

wherein Q represents C(R) or N; Q$^1$ represents C(R$^1$) or N; R represents a hydrogen atom, a halogen atom, an alkyl group having 1 to 6 carbon atoms, or a carboxyl group, where two Rs may bind to each other to form a ring; R$^1$ represents a hydrogen atom, a halogen atom, an alkyl group having 1 to 6 carbon atoms, or a carboxyl group, where two R$^1$s may bind to each other to form a ring; n represents a number of 0 to 3; and m represents a number of 0 to 3.

2. The compound according to claim 1, wherein Q and Q$^1$ in the general formula (1) respectively represent C(R) and C(R$^1$).

3. The compound according to claim 1, wherein each of Q and Q$^1$ in the general formula (1) represents N.

4. A method for producing a compound represented by a general formula (6), comprising:
obtaining a compound represented by a general formula (5) by reacting 8-hydroxyjulolidine with a compound represented by a general formula (4); and
reacting the compound represented by the general formula (5) with hydroquinone in the presence of a condensing agent,

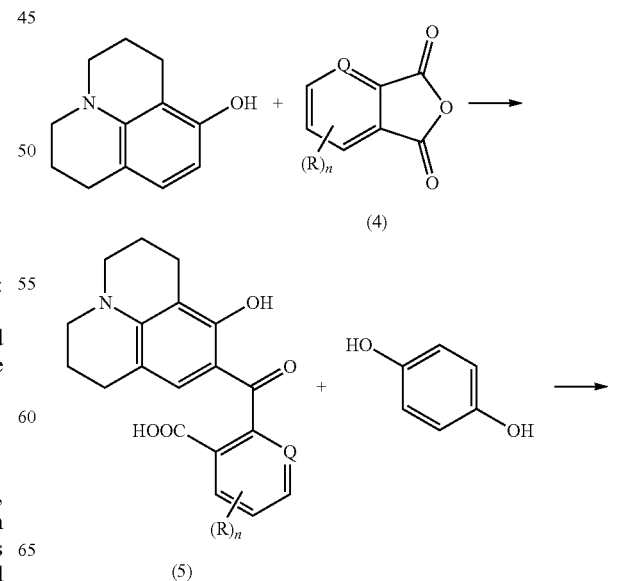

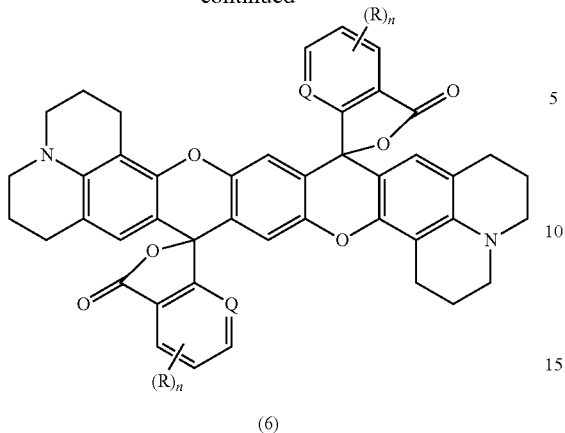

(6)

wherein Q represents C(R) or N; R represents a hydrogen atom, a halogen atom, an alkyl group having 1 to 6 carbon atoms, or a carboxyl group, where two Rs may bind to each other to form a ring; and n represents a number of 0 to 3.

5. A compound that exhibits different changes in hue, said compound represented by the following formula (1):

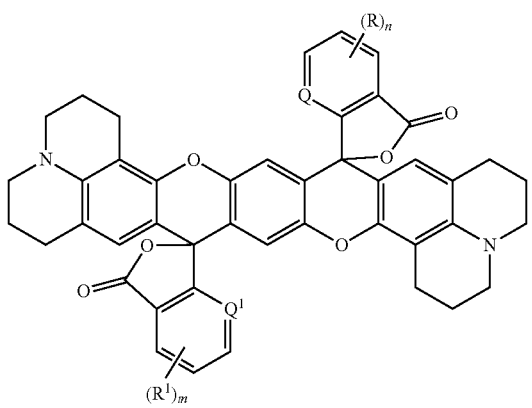

(1)

wherein Q represents C(R) or N; $Q^1$ represents $C(R^1)$ or N; R represents a hydrogen atom, a halogen atom, an alkyl group having 1 to 6 carbon atoms, or a carboxyl group, where two Rs may bind to each other to form a ring; $R^1$ represents a hydrogen atom, a halogen atom, an alkyl group having 1 to 6 carbon atoms, or a carboxyl group, where two $R^1$s may bind to each other to form a ring; n represents a number of 0 to 3; and m represents a number of 0 to 3,
wherein the compound is in a neutral form, monocationic form or dicationic form, thereby to exhibit different changes in hue depending on in which form the compound is.

6. The compound according to claim 5, wherein the compound is used for detecting phenols and for fluorescence imaging.

* * * * *